(12) United States Patent
Yamaguchi

(10) Patent No.: US 9,551,022 B2
(45) Date of Patent: Jan. 24, 2017

(54) DUAL SURFACTANT ENZYMATIC METHOD FOR MEASURING A SUBSTRATE IN A BLOOD SAMPLE

(71) Applicant: SEKISUI MEDICAL CO., LTD., Chuo-ku (JP)

(72) Inventor: Toyomi Yamaguchi, Ibaraki (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 0 days.

(21) Appl. No.: 14/389,510

(22) PCT Filed: Apr. 1, 2013

(86) PCT No.: PCT/JP2013/060015
§ 371 (c)(1),
(2) Date: Sep. 30, 2014

(87) PCT Pub. No.: WO2013/147309
PCT Pub. Date: Oct. 3, 2013

(65) Prior Publication Data
US 2015/0072367 A1   Mar. 12, 2015

(30) Foreign Application Priority Data
Mar. 30, 2012 (JP) ................................ 2012-082977

(51) Int. Cl.
*C12Q 1/28* (2006.01)
*C12Q 1/26* (2006.01)

(52) U.S. Cl.
CPC .. *C12Q 1/28* (2013.01); *C12Q 1/26* (2013.01)

(58) Field of Classification Search
CPC .................................... C12Q 1/26; C12Q 1/28
USPC .......................................................... 435/28
See application file for complete search history.

(56) References Cited

U.S. PATENT DOCUMENTS

| | | | |
|---|---|---|---|
| 5,073,368 A | 12/1991 | Subramanian | |
| 5,384,248 A | 1/1995 | Sakata et al. | |
| 5,559,003 A | 9/1996 | Kawahara et al. | |
| 5,639,630 A | 6/1997 | Malin et al. | |
| 2005/0048592 A1 | 3/2005 | Wood et al. | |
| 2007/0026523 A1* | 2/2007 | Taniguchi | C12Q 1/37 436/18 |
| 2010/0255516 A1* | 10/2010 | Itoh | G01N 33/92 435/11 |

FOREIGN PATENT DOCUMENTS

| | | |
|---|---|---|
| CN | 1492936 | 4/2004 |
| EP | 0 402 094 | 12/1990 |
| EP | 0 657 545 | 6/1995 |
| EP | 1 386 971 | 2/2004 |
| EP | 2 208 794 A1 | 7/2010 |
| JP | 03-010696 A | 1/1991 |
| JP | 07-039394 A | 2/1995 |
| JP | 07-051095 A | 2/1995 |
| JP | 07051095 A * | 2/1995 |
| JP | 07-155196 A | 6/1995 |
| JP | 08-308593 A | 11/1996 |
| JP | 2000-83698 | 3/2000 |
| JP | 2000-93200 | 4/2000 |
| JP | 2000-189194 | 7/2000 |
| JP | 2006-081471 A | 3/2006 |
| WO | WO 02/27331 | 4/2002 |
| WO | WO 2011/088383 A1 | 7/2011 |

OTHER PUBLICATIONS

Chinese Office Action issued Jul. 28, 2015 in connection with corresponding Chinese Patent Application No. 201380017615.9, filed Apr. 1, 2013.
Extended European Search Report issued Aug. 24, 2015 in Patent Application No. 13767986.6.
International Search Report issued Jul. 2, 2013 in PCT/JP2013/060015 filed Apr. 1, 2013.
Office Action issued Nov. 29, 2016, in Japanese patent application No. 2015-055780 (w/ English translation).

* cited by examiner

*Primary Examiner* — Scott Long
*Assistant Examiner* — Paul Martin
(74) *Attorney, Agent, or Firm* — Oblon, McClelland, Maier & Neustadt, L.L.P.

(57) ABSTRACT

Provided is a method for measuring a substance in a blood sample, which allows avoidance of the influences of both of bilirubin and hemoglobin by simple operations.
Provided is a method for measuring a substance in a blood sample by an enzymatic method using an oxidizable color reagent, the method including (1) bringing the blood sample into contact with a non-ionic surfactant; and then (2) bringing the resultant sample into contact with a betaine-type amphoteric surfactant, to perform an enzyme reaction and a color reaction by an oxidizable color reagent at the same time as the contact or after the contact.

14 Claims, 4 Drawing Sheets

DUAL SURFACTANT ENZYMATIC METHOD FOR MEASURING A SUBSTRATE IN A BLOOD SAMPLE

FIELD OF THE INVENTION

The present invention relates to a method for measuring a substance in a blood sample by an enzymatic method using an oxidizable color reagent.

BACKGROUND OF THE INVENTION

Measurement of the concentration of various substances in a blood sample is important for diagnosis of various diseases or judgment of the treatment process. For example, measurement of substances such as cholesterol, uric acid, glucose, triglyceride, phospholipid, choline, creatine, creatinine, free cholesterol, and cholesterol ester in the blood is important. As a method for measuring them, widely used is a method (enzymatic method using an oxidizable color reagent) in which an oxidase is applied to these components or a derivative of these components, and hydrogen peroxide generated directly or indirectly from the enzymatic reaction is applied to an oxidizable color reagent, which is a coloring reagent of the hydrogen peroxide, and then the generated color is quantified.

However, reducing substances such as bilirubin, hemoglobin, and ascorbic acid exist in a blood sample, and existence of these substance greatly affect measurement values of the substances in the blood sample, which may cause errors in the measurement values. In addition, it is known that, for example, bilirubin or hemoglobin which also acts as a coloring matter causes errors depending on a measurement wavelength, and absorption of these coloring matters themselves temporally changes during the measurement because of the existence of, for example, light and components in the measurement reagent, and affects the measurement results.

As a method for avoiding the influences of bilirubin, among the above components, known is a method in which an amphoteric surfactant is added to a measurement reagent. For example, Patent Literature 1 describes that an amphoteric surfactant is added to a first reagent for the purpose of avoiding the influences of bilirubin. Patent Literature 2 describes a method for measuring a bio-component by detection of hydrogen peroxide produced from the enzymatic reaction with peroxidase and an oxidizable coloring agent in which an amphoteric surfactant and a ferrocyanide compound are allowed to exist together with a first reagent or both of the first reagent and a second reagent.

Further, Patent Literature 3 describes a method for measuring a substrate or an enzyme activity in the body fluid, in which an amphoteric surfactant (only alkyl betaine oxide (product name: AMPHITOL 20N) as used in Examples) is allowed to co-exist with a first reagent or a second reagent in a measurement system for the purpose of avoiding the influences of hemoglobin or/and bilirubin existing in the body fluid. However, in Patent Literature 3, there is no Example investigating the influences of both of total hemoglobin and bilirubin in the reagent at the same time under existence of the amphoteric surfactant. In addition, Patent Literature 4 describes a method using a peroxide and a non-ionic surfactant or/and an amphoteric ion surfactant as a method for avoiding the influences of both of hemoglobin and bilirubin. However, in Patent Literature 4, adjustment of the reagent is complicated such that the surfactant needs to be treated with, for example, light irradiation, and the peroxide concentration needs to be adjusted to a certain quantity.

CITATION LIST

Patent Literature

Patent Literature 1: JPH07-039394 A
Patent Literature 2: JPH07-155196 A
Patent Literature 3: JPH03-010696 A
Patent Literature 4: JP 2006-081471 A

SUMMARY OF THE INVENTION

Problem to be Solved by the Invention

The present inventors found that when an amphoteric surfactant was used for the measurement reagent as described in Patent Literatures 1 and 2 for the purpose of avoiding the influences of bilirubin, the measurement value sometimes deviated from the expectation value in a hemolysis specimen. The present inventors investigated this mechanism, and revealed that the amphoteric surfactant changes the absorption spectrum of hemoglobin.

Accordingly, the problem of the invention is to provide a method for measuring a substance in a blood sample, which allows avoidance of the influences of both of bilirubin and hemoglobin at the same time by simple operations.

Means for Solving the Problem

The present inventors investigated the effects of adding various surfactants to solve the problems described above, and found that the effects of avoiding the influences of bilirubin and hemoglobin are greatly different depending on the kind of the surfactants, and also greatly different depending on the timing of adding the surfactants to the measurement system. The present inventors further investigated based on the findings described above, and found that by first bringing a blood sample into contact with a non-ionic surfactant, and then bringing this sample into contact with a betaine-type amphoteric surfactant at the time of the enzymatic reaction, it is possible to avoid the influences of both of bilirubin and hemoglobin at the same time, and completed the invention.

Specifically, the invention provides a method for measuring a substance in a blood sample by an enzymatic method using an oxidizable color reagent, which is characterized by (1) bringing the blood sample into contact with a non-ionic surfactant, and then (2) bringing the resultant sample into contact with a betaine-type amphoteric surfactant, to perform an enzymatic reaction and a color reaction by an oxidizable color reagent at the same time as the contact or after the contact.

In addition, the invention provides an enzymatic-method measurement reagent including (A) a first reagent containing a non-ionic surfactant, (B) a betaine-type amphoteric surfactant, (C) an oxidase specific for an object to be measured or a derivative thereof and (D) an oxidizable color reagent.

Effects of the Invention

According to the method of the invention, it is possible to avoid the influences of bilirubin and hemoglobin at the same time, which widely exists in a blood sample, and it is possible to exactly measure various substances in a blood sample only by adding two kinds of surfactants, respectively.

DETAILED DESCRIPTION OF THE INVENTION

Figure 1:
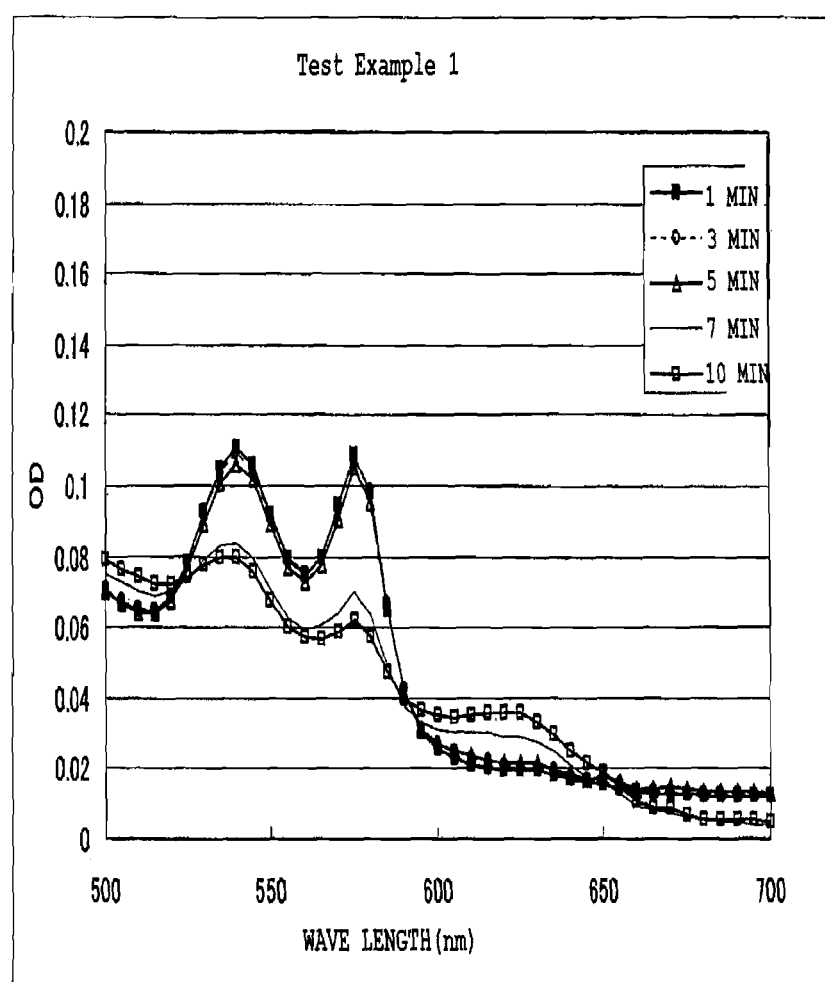
FIG. 1 shows the temporal change of the absorption spectrum of hemoglobin, when to a hemoglobin-added serum a buffer solution not containing a surfactant is added and reacted at 37° C. for 5 minutes, and then a buffer solution containing an amphoteric surfactant is added and reacted at 37° C. for 5 minutes.

A method for measuring a substance in a blood sample of the invention is characterized by (1) bringing the blood sample into contact with a non-ionic surfactant (the first process); and then (2) bringing the resultant sample into contact with a betaine-type amphoteric surfactant, to perform an enzymatic reaction and a color reaction by an oxidizable color reagent at the same time as the contact or after the contact (the second process); in which the other operations are performed in accordance with an ordinary enzymatic method using an oxidizable color reagent.

Examples of the blood sample used in the first process include a blood plasma, a serum, and urine. Among them, the blood sample is more preferably the blood plasma or the serum, which is highly likely to cause the influences of hemoglobin and bilirubin on a measurement value.

Examples of the substance that is an object to be measured in a blood sample (test substance) include substances other than hemoglobin and bilirubin in a blood sample, for example, uric acid, creatinine, cholesterol, triglyceride, polyamine, bile acid, 1,5-anhydroglucitol, pyruvic acid, lactic acid, phospholipid, urea, glucose, choline, creatine, and free fatty acid. However, the test substance is not particularly limited thereto, and any body fluid that can be measured by quantifying hydrogen peroxide produced from the enzymatic reaction, can be measured.

The first process of the invention is a process of bringing a non-ionic surfactant into contact with a blood sample before performing an oxidase reaction with respect to the test substance. It is important to use a non-ionic surfactant in the first process in the invention, and in a case where a betaine-type amphoteric surfactant is used in the first process, or in a case where a betaine-type amphoteric surfactant is used both in the first process and in the second process, it is not possible to avoid the influences of both of hemoglobin and bilirubin. A means for bringing the non-ionic surfactant into contact with the blood sample may be addition of the non-ionic surfactant to the blood sample, or may be incorporation of the non-ionic surfactant into a diluent solution of the blood sample, or may be use of a solution containing the non-ionic surfactant as a pre-treatment solution of the blood sample. As the pre-treatment solution of the blood sample (also referred to as a first reagent), a solution containing a non-ionic surfactant is preferably used.

The non-ionic surfactant used in the invention is suitably polyoxyethylene polyoxypropylene condensates (POE/POP condensates), polyoxyethylene alkyl ethers, polyoxyethylene alkyl phenyl ethers or polyoxyethylene polyalcohol fatty acid ester.

Examples of the POE/POP condensates include those represented by Formulae (1) to (5) described below. (a) POE/POP condensate represented by Formula (1) described below.

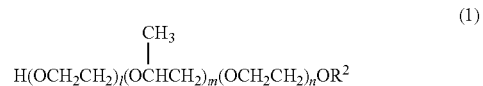

(1)

In Formula (1), l and n represent the average addition mole number of ethylene oxide, and m represents the average addition mole number of propylene oxide, and l and n are each a number of from 0 to 250, l+n is 1 or more, and m is a number of from 1 to 250. l+n is preferably from 10 to 300 and m is preferably from 10 to 100. l and n may be the same or different. $R^2$ represents a hydrogen atom or an alkyl group having from 2 to 20 carbon atoms.

(b) Polyoxyethylene polyoxypropylene alkyl amine condensate or polyoxyethylene polyoxypropylene diamine condensate represented by Formulae (2) to (5) described below.

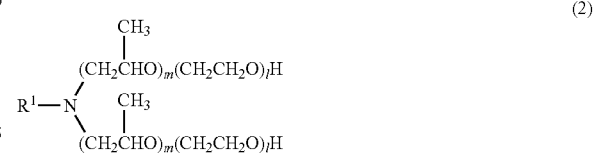

(2)

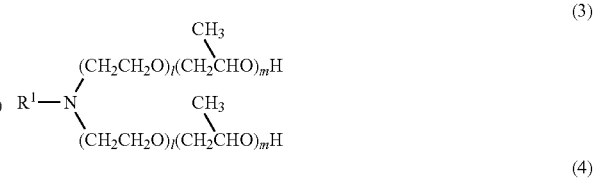

(3)

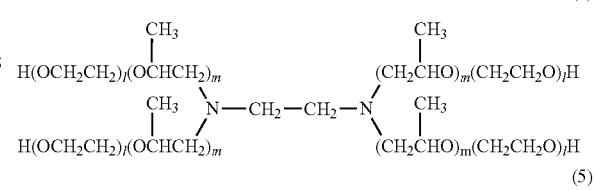

(4)

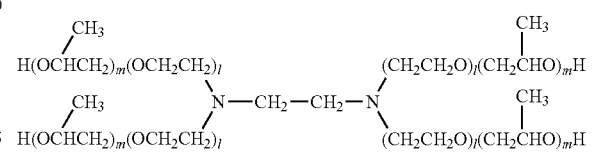

(5)

(wherein $R^1$ represents an alkyl group having from 2 to 20 carbon atoms, l represents a number of from 1 to 150 and m represents a number of from 1 to 100)

As a commercial product of the POE/POP condensate of Formula (1), PLURONIC® (registered trademark, the same shall apply hereinafter, PLURONIC® types are block copolymers based on ethylene oxide and propylene oxide) F-108 (EO300/PO50) or PLURONIC® P-85 (EO54/PO39) may be suitably used.

As the POE/POP alkyl amine condensate or POE/POP diamine condensate of Formula (2) or Formula (3), PLURONIC® TR-704 (a molecular weight of 5000, 40 mass % of EO content) or PLURONIC® TR-702 (a molecular weight of 3500, 20 mass % of EO content) may be suitably used.

l, m and n described above represent the average values of those usually having a distribution to some extent, but the distribution may be preferably a distribution within ±20%, more preferably a distribution within ±10%, and further preferably a distribution within ±5%.

Examples of the polyoxyethylene alkyl ethers include polyoxyethylene $C_{10}$-$C_{24}$ alkyl ethers having 5 to 80 of POE addition mole number. Examples of the preferably used commercial product of the polyoxyethylene alkyl ethers include NIKKOL (registered trademark, the same shall apply hereinafter) BL-25 (manufactured by Nikko Chemicals Co., Ltd., POE (25) lauryl (C12) ether), EMULGEN (registered trademark, the same shall apply hereinafter) 220 (manufactured by Kao Corporation, POE (13) cetyl (C16) ether), NIKKOL BT-9 (manufactured by Nikko Chemicals Co., Ltd., POE (9) oleyl (C18) ether, $C_{15}H_{31}O(CH_2CH_2O)_9H$) and EMULGEN 420 (manufactured by Kao Corporation, POE (13) oleyl (C18) ether) may be suitably used. More suitable range of the POE addition mole number is 8 to 30.

Examples of the polyoxyethylene alkyl phenyl ether include $C_6$-$C_{18}$ alkyl phenyl ethers having from 5 to 80 of the POE addition mole number. Examples of the preferably used commercial product of the polyoxyethylene alkyl phenyl ether include NIKKOL NP-10 (manufactured by Nikko Chemicals Co., Ltd., POE (10) nonyl (C10) phenyl ether), NIKKOL NP-15 (manufactured by Nikko Chemicals Co., Ltd., POE (15) nonyl (C10) phenyl ether), NIKKOL NP-20 (manufactured by Nikko Chemicals Co., Ltd., POE (20) nonyl (C10) phenyl ether), Noigen EA-143 (manufactured by DAI-ICHI KOGYO SEIYAKU CO., LTD., POE (8) dodecyl (C12) phenyl ether) and TritonX-100 (manufactured by Sigma-Aldrich Co. LLC., POE (9.5) octyl (C8) phenyl ether) may be suitably used.

Examples of the polyoxyethylene polyalcohol fatty acid ester include polyoxyethylene sorbitan fatty acid esters, polyoxyethylene glycerin fatty acid esters, and polyoxyethylene pentaerythritol fatty acid esters. Among them, the polyoxyethylene polyalcohol fatty acid ester is preferably a polyoxyethylene polyalcohol fatty acid ester having from 30 to 60 of the POE addition mole number, more preferably a polyoxyethylene sorbitan fatty acid ester having from 3 to 60 of the POE addition mole number, and is preferably a polyoxyethylene sorbitan $C_8$-$C_{24}$ fatty acid ester having from 3 to 60 of the POE addition mole number.

As a commercial product of the polyoxyethylene polyalcohol fatty acid ester, Tween 20 (registered trademark) (polyoxyethylene sorbitan monolaurate (C12)) may be suitably used.

Among these non-ionic surfactants, the non-ionic surfactant is more preferably polyoxyethylene polyoxypropylene condensates (POE/POP condensates), and further preferably POE/POP condensates, POE/POP alkyl amine condensates or POE/POP diamine condensates.

The non-ionic surfactant is preferably used in from 0.1 to 10 w/v %, further preferably from 0.5 to 10 w/v %, and further more preferably from 0.5 to 1.0 w/v % as a concentration after contact with the blood sample in the point of avoiding the influences of both of hemoglobin and bilirubin. The reagent of the invention is applied to a biochemical automatic analysis device in the field of clinical laboratory test where the method of the invention is suitably used. In the biochemical automatic analysis device, the volume ratio of the blood sample/the first reagent/the second reagent is often in a range of from 1 to 10 μL/from 50 to 300 μL/from 20 to 200 μL respectively, and the volume ratio of the first reagent and the second reagent is often 1:1 to 5:1. Accordingly, the concentration of the non-ionic surfactant after contact with the blood sample is slightly different from the concentration of the non-ionic surfactant in the first reagent due to the dilution, but the second reagent is further added to the mixture of the blood sample and the first reagent, and thus it is complicated to indicate the concentration of the amphoteric surfactant by the concentration in the reaction system. From this, the concentration of the amphoteric surfactant in the present specification is indicated by the concentration in the reagent containing an amphoteric surfactant. The concentration of the amphoteric surfactant can be set up to be suitable for the measurement system of the desired sample/reagent volume ratio from those described above by a person having ordinary skill in the art.

The contact of blood sample and the non-ionic surfactant is preferably performed by, for example, adding a solution containing the non-ionic surfactant to the blood sample, and then standing or incubating the blood sample at 30 to 40° C. for 1 minute to 10 minutes, and further preferably at 37° C. for 5 minutes.

The second process of the invention is to bring a betaine-type amphoteric surfactant into contact with the blood sample that has been brought into contact with the non-ionic surfactant, to perform an enzymatic reaction and a color reaction by an oxidizable color reagent at the same time as the contact or after the contact.

The surfactant used in the second process is a betaine-type amphoteric surfactant. If an amine oxide-type amphoteric surfactant such as lauryl dimethylamine oxide as described in Example 3 of Patent Literature 2 is used in this second process, the influences of hemoglobin cannot be avoided although the influences of bilirubin can be avoided. Examples of the betaine-type amphoteric surfactant to be used include alkyl betaines ($R^3N^+(CH_3)_2CH_2COO^-$), amidoalkyl betaines ($R^3CONH(CH_2)_3N(CH_3)_2CH_2COO^-$), sulfobetaines ($R^3CONH(CH_2)_3N^+(CH_3)_2CH_2CH(OH)CH_2SO_3^-$), and 2-alkyl-N-carboxymethyl-N-hydroxyethylimidazolinium betaines ($R^3C_3H_4N_2(C_2H_{40}H)CH_2COO^-$) (herein $R^3$ represents a $C_8$-$C_{24}$ alkyl group). Among them, the betaine-type amphoteric surfactant is more preferably an alkyl betaine and an amidoalkyl betaine.

Examples of a commercial product of the betaine-type amphoteric surfactant include, for example, AMPHITOL 24B (manufactured by Kao Corporation, lauryl betaine, CAS No. 683-10-3) as an alkyl betaine derivative, and ENAGICOL C-30B (manufactured by Lion Corporation, coconut oil fatty acid amidoalkyl betaine, CAS No. 61789-40-0) as an amidoalkyl betaine derivative.

A suitable concentration of the betaine-type amphoteric surfactant is exemplified by a concentration in the reagent containing the betaine-type amphoteric surfactant. The betaine-type amphoteric surfactant is preferably used in from 0.5 to 10 w/v %, and further from 2.0 to 10 w/v % as the concentration in the reagent in the point of avoiding the influences of both of hemoglobin and bilirubin. In addition, the concentration of the betaine-type amphoteric surfactant may be preferably from 0.5 to 2.0 w/v % depending on the concentration of the non-ionic surfactant.

The contact of the betaine-type amphoteric surfactant and the blood sample is be performed by the addition of the betaine-type amphoteric surfactant to the blood sample which was allowed after contact with the non-ionic surfactant. The enzymatic reaction may be performed either at the same time as or after the contact of the blood sample with the betaine-type amphoteric surfactant. Accordingly, the betaine-type amphoteric surfactant may be added to a sample containing one or more enzymes (the second reagent).

When the measurement system (reagent system) is constituted with a two-reagent system formed by the first reagent and the second reagent, which is one embodiment of the invention, it is preferred to incorporate the non-ionic surfactant into the first reagent and the betaine-type amphoteric surfactant into the second reagent, so that the concentration of the non-ionic surfactant after the contact with the blood sample is 0.5 to 1.0 w/v % and the concentration of the betain-type amphoteric surfactant in the reagent is 2.0 to 10 w/v %.

Examples of the enzyme used in the measurement of the substance to be measured in a blood sample to which the system of the invention is applied, include oxidation enzymes specific for the object to be measured or a derivative thereof, for example, uric acid (uricase, peroxidase), creatinine (creatininase, creatinase, sarcosine oxidase, peroxidase), cholesterol (cholesterol oxidase, peroxidase), triglyceride (lipoprotein lipase, glycerol kinase, glycerol-3-phosphoric acid oxidase, peroxidase), polyamine (polyamine amidohydrolase, polyamine oxidase, putrescine oxidase, peroxidase), bile acid (3-α-hydroxysteroid dehydrogenase, diaphorase, peroxidase), 1,5-anhydroglucitol (1,5-anhydroglucitoloxidase, pyranose oxidase, peroxidase), pyruvic acid (pyruvic acid oxidase, peroxidase), lactic acid (lactic acid oxidase, peroxidase), phospholipid (phospholipase D, choline oxidase, peroxidase), and urea (ureaamidolyase, pyruvate kinase, pyruvic acid oxidase, peroxidase).

The oxidizable color reagent may be one kind or two or more kinds of components which are colored by the reaction with hydrogen peroxide, and examples thereof include combinations of 4-aminoantipyrine and a phenol-based, a naphthol-based or an aniline-based compound; combinations of 3-methyl-2-benzothiazolinone hydrazone and an aniline-based compound; triphenyl methane-based leuco dyes; diphenyl amine derivatives; benzidine derivatives; triallyl imidazole derivatives; leucomethylene blue derivatives; or O-phenylene diamine derivatives.

The second process is usually performed at 30 to 40° C. for 1 minute to 10 minutes, and preferably at 37° C. for 5 minutes. For pH adjustment, for example, phosphoric acid salts, citric acid salts, boric acid salts, carbonic acid salts, Tris buffer, and Good's buffer are used. Measurement of the color by the second process is performed by optically quantifying the coloring of the color reagent.

According to the invention method, it is possible to avoid the influences of hemoglobin and bilirubin contained in a blood sample on the measurement value, and to exactly determine the quantity of a test substance.

The measurement reagent for implementing the method of the invention is preferably an enzymatic method measurement reagent comprising (A) a first reagent containing a non-ionic surfactant, (B) a betaine-type amphoteric surfactant, (C) an oxidase specific for an object to be measured or a derivative thereof and (D) an oxidizable color reagent.

Preferred embodiments of the invention are illustrated below.

[1] A method for measuring a substance in a blood sample by an enzymatic method using an oxidizable color reagent, which is characterized by (1) bringing the blood sample into contact with a non-ionic surfactant; and then (2) bringing the resultant sample into contact with a betaine-type amphoteric surfactant, to perform an enzyme reaction and a color reaction by an oxidizable color reagent at the same time as the contact or after the contact.

[2] The method according to [1], wherein the blood sample is a blood plasma or a serum that is highly likely to cause the influences of hemoglobin and bilirubin on a measurement value.

[3] The method according to [1] or [2], wherein the substance in the blood sample is a substance in a blood sample that can be measured by quantifying hydrogen peroxide produced by the enzyme reaction, and is neither hemoglobin nor bilirubin, and more preferably a substance selected from uric acid, creatinine, cholesterol, triglyceride, polyamine, bile acid, 1,5-anhydroglucitol, pyruvic acid, lactic acid, phospholipid, urea, glucose, choline, creatine and free fatty acid.

[4] The method according to any one of [1] to [3], wherein the non-ionic surfactant is one kind, or two or more kinds selected from the group consisting of polyoxyethylene polyoxypropylene condensates (POE/POP condensates), polyoxyethylene alkyl ethers, polyoxyethylene alkyl phenyl ethers and polyoxyethylene polyalcohol fatty acid esters, more preferably one kind, or two or more kinds selected from the group consisting of POE/POP condensates, POE/POP alkyl amine condensates or POE/POP diamine condensates.

[5] The method according to any one of [1] to [4], wherein the use amount of the non-ionic surfactant is an amount to render the concentration after contact with the blood sample to be from 0.1 to 10 w/v %, more preferably from 0.5 to 10 w/v %.

[6] The method according to any one of [1] to [5], wherein the betaine-type amphoteric surfactant is one kind, or two or more kinds selected from the group consisting of alkyl betaines, amidoalkyl betaines, sulfobetaines and 2-alkyl-N-carboxymethyl-N-hydroxyethylimidazolium betaines, more preferably one kind, or two or more kinds selected from the group consisting of alkyl betaines and amidoalkyl betaines.

[7] The method according to any one of [1] to [6], wherein the use amount of the betaine-type surfactant is an amount to render the concentration in the reagent to be from 0.5 to 10 w/v %.

[8] The method according to any one of [1] to [7], wherein the enzyme is an oxidase specific for an object to be measured or a derivative thereof.

[9] The method according to any one of [1] to [8], wherein the oxidizable color reagent is one kind or two or more kinds of a component which is colored by the reaction with hydrogen peroxide.

[10] The method according to any one of [1] to [9], which is a method for avoiding the influences of hemoglobin and bilirubin in the blood sample on a measurement value.

[11] An enzymatic method measurement reagent, which is characterized by comprising (A) a first reagent containing a non-ionic surfactant, (B) a betaine-type amphoteric surfactant, (C) an oxidase specific for an object to be measured or a derivative thereof and (D) a second reagent containing an oxidizable color reagent.

EXAMPLES

The invention is described in more detail with examples below.

Test Examples

Using the first reagent and the second reagent having the compositions described in Table 1 below, the absorption spectrum of hemoglobin in a sample to be measured was measured.

TABLE 1

|  | First reagent | Second reagent |
|---|---|---|
| Test Example 1 | MES buffer solution 75 mmol/L (pH 7.0) | MES buffer solution 75 mmol/L (pH 7.0) AMPHITOL 24B 2 w/v % |
| Test Example 2 | MES buffer solution 75 mmol/L (pH 7.0) AMPHITOL 24B 2 w/v % | MES buffer solution 75 mmol/L (pH 7.0) |
| Test Example 3 | MES buffer solution 75 mmol/L (pH 7.0) AMPHITOL 24B 2 w/v % | MES buffer solution 75 mmol/L (pH 7.0) AMPHITOL 24B 2 w/v % |

(Sample for Measurement)

The hemoglobin (derived from hemocyte) was added in 500 mg/dL to the pool serum, to prepare a hemoglobin-added serum.

(Measurement Method)

Hitachi U3310 model spectrophotometer (manufactured by Hitachi, Ltd.) was used, and the first reaction and the second reaction were performed, respectively in a liquid volume ratio of 45 µL of the sample to be measured, 1.8 mL of the first reagent and 0.9 mL of the second reagent at 37° C. for 5 minutes, and the absorption spectrum of hemoglobin was measured. Meanwhile, after the second reaction (7 minutes, 10 minutes), correction for the liquid volume was performed in consideration of the dilution ratio.

(Results)

Figure 2:
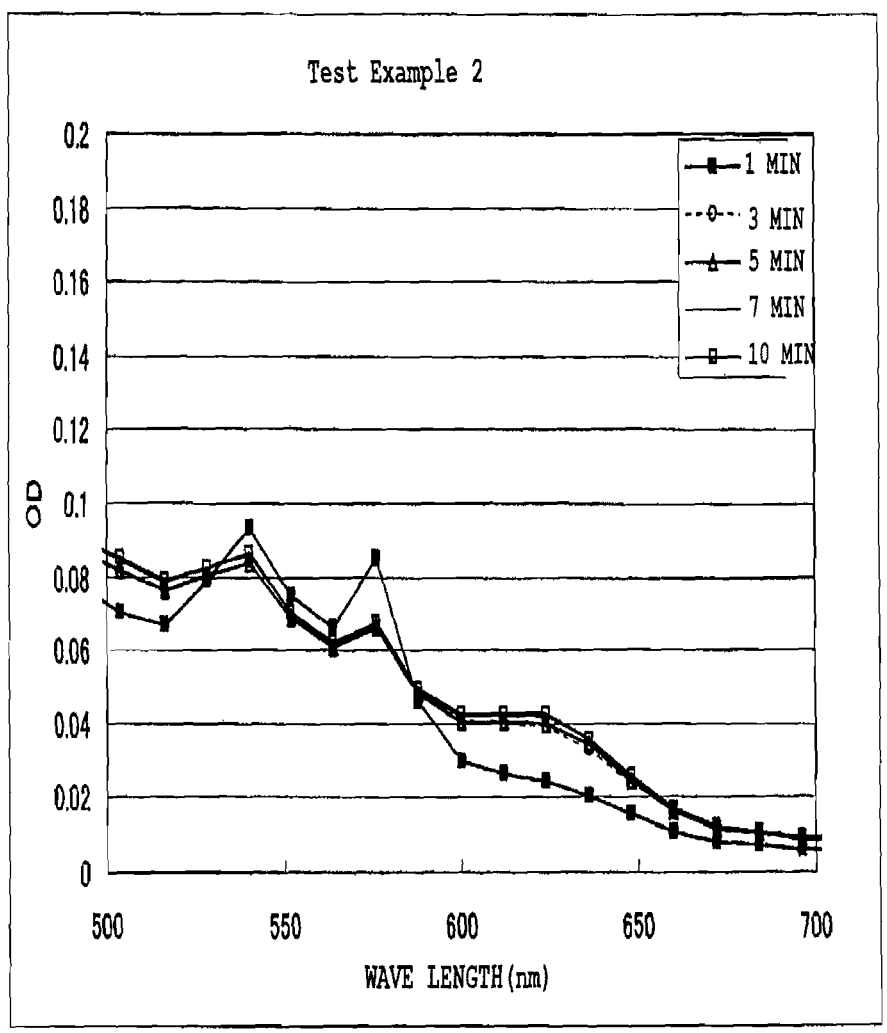
FIG. 2 shows the temporal change of the absorption spectrum of hemoglobin, when to a hemoglobin-added serum a buffer solution containing an amphoteric surfactant is added and reacted at 37° C. for 5 minutes, and then a buffer solution not containing a surfactant is added and reacted at 37° C. for 5 minutes.
Figure 3:
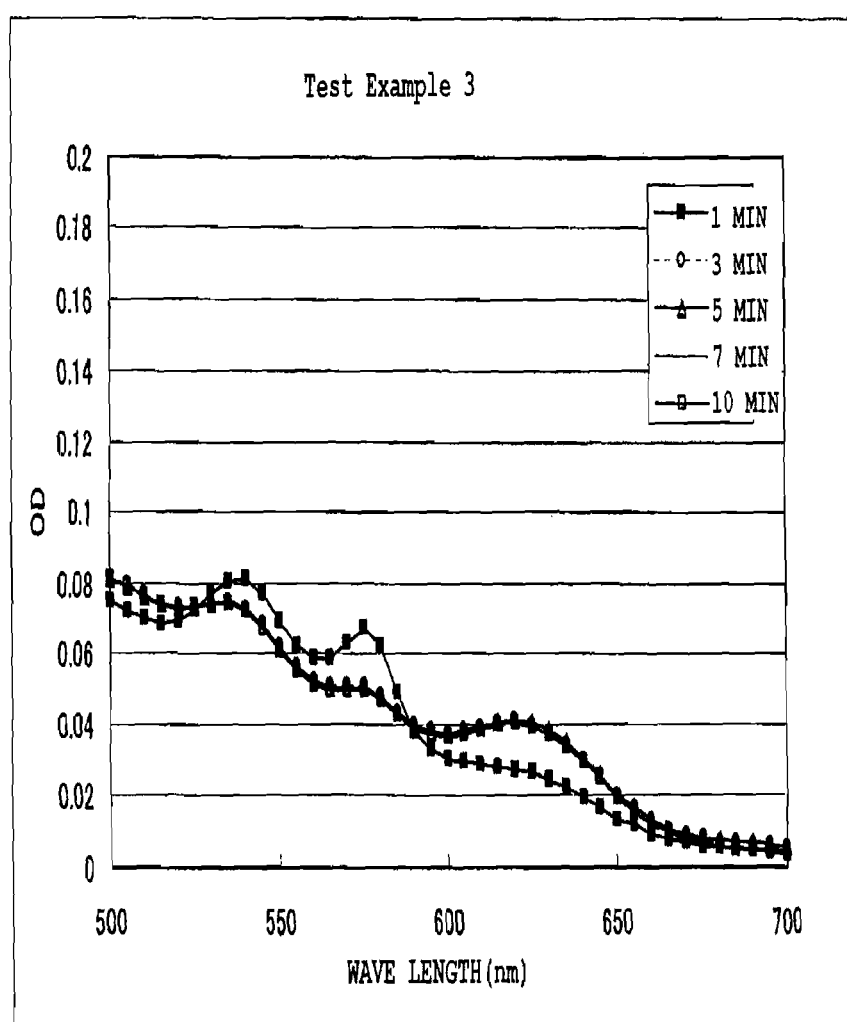
FIG. 3 shows the temporal change of the absorption spectrum of hemoglobin, when to a hemoglobin-added serum a buffer solution containing an amphoteric surfactant is added and reacted at 37° C. for 5 minutes, and then a buffer solution containing an amphoteric surfactant is further added and reacted at 37° C. for 5 minutes.

The hemoglobin has characteristic peaks around 540 nm and 575 nm, and if the characteristics of the hemoglobin changes, the shape of the peaks changes. In Example 1, the shape of the peaks did not change in the first reaction, but the peaks collapsed after initiation of the second reaction and began to change to a gentle shape. In Examples 2 and 3, the hemoglobin-characteristic peaks were recognized at 1 minute after initiation of the first reaction, but the peaks collapsed after 3 minutes, and the spectrum did not greatly change in the second reaction. From these results, it was found that AMPHITOL 24B has an action of changing the spectrum of the hemoglobin (FIG. 1 to FIG. 3).

Example 1

Using the first reagent and the second reagent respectively having the contents described in Table 2 below, the absorption spectra of hemoglobin in a sample to be measured were measured.

TABLE 2

|  | First reagent | Second reagent |
|---|---|---|
| Example 1 | MES buffer solution 75 mmol/L (pH 7.0) Pluronic TR-704 2 w/v % | MES buffer solution 75 mmol/L (pH 7.0) AMPHITOL 24B 2 w/v % |

(Sample for Measurement)

The hemoglobin (derived from hemocyte) was added in 500 mg/dL to the pool serum, to prepare a hemoglobin-added serum.

(Measurement Method)

Hitachi U3310 model spectrophotometer (manufactured by Hitachi, Ltd.) was used, and the first reaction and the second reaction were performed, respectively at 37° C. for 5 minutes, in a liquid volume ratio of 45 µL of the sample to be measured, 1.8 mL of the first reagent and 0.9 mL of the second reagent, and the absorption spectra of hemoglobin were measured. Furthermore, after the second reaction (at 7 minutes, and at 10 minutes), correction for the liquid volume was performed in consideration of the dilution ratio.

(Results)

Figure 4:
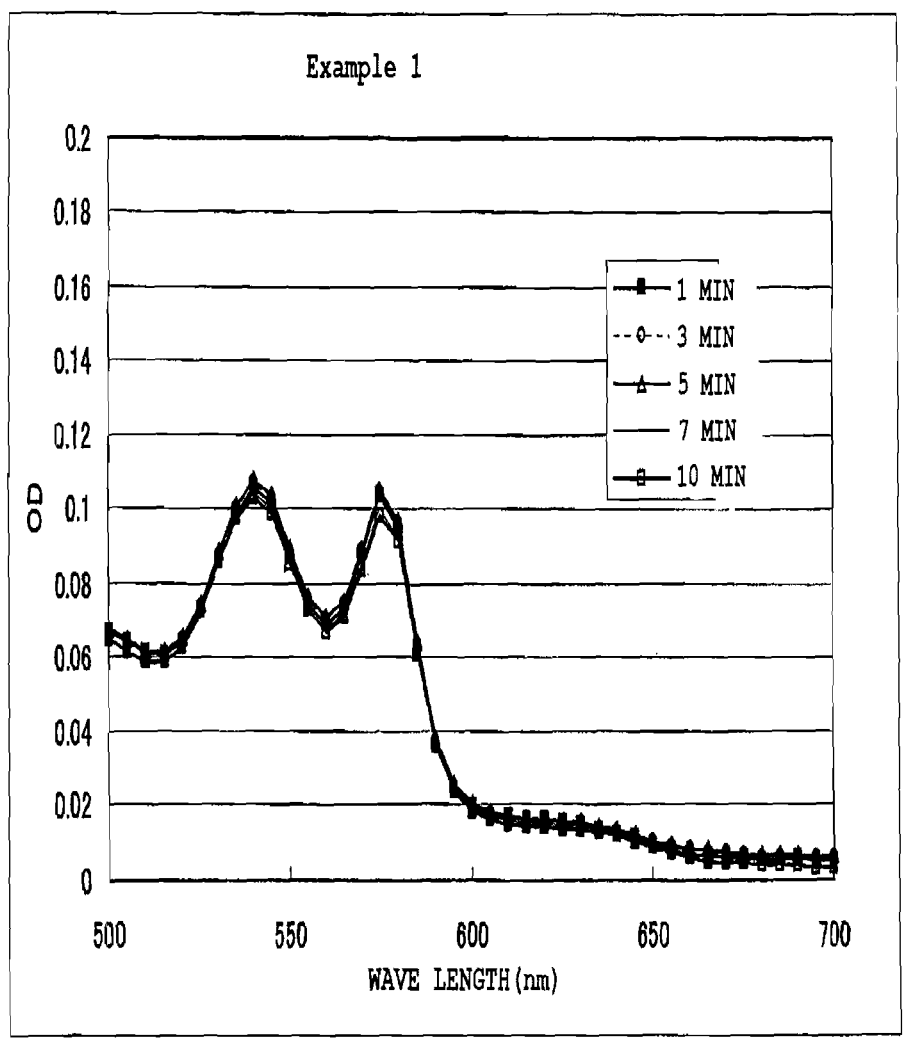
FIG. 4 shows the temporal change of the absorption spectrum of hemoglobin, when to a hemoglobin-added serum a buffer solution containing a non-ionic surfactant is added and reacted at 37° C. for 5 minutes, and then a buffer solution containing an amphoteric surfactant is added and reacted at 37° C. for 5 minutes.

In Example 1, the shape of the peaks around 540 and 575, which is characteristic for hemoglobin, did not change in any of the first reaction and the second reaction (FIG. 4).

Example 2

The effects of the invention were confirmed using a uric acid-measurement system.

The combinations described in Table 3 were used as the surfactants prescribed as the first reagent and the second reagent, and the measurement reagents of Example 2 and Comparative Examples 1 to 4 were prepared.

(First Reagent)

MES buffer solution 75 mmol/L (pH 7.0)

TOOS (Manufacturer: Dojindo Molecular Technologies, Inc., Catalog number: OC13) 0.75 mmol/L POD (Manufacturer: TOYOBO CO., LTD., Catalog number: PEO-301) 3 U/mL Surfactant 2.0 w/v %

PLURONIC® TR-704 (Manufacturer: ADEKA CORPORATION, CAS No. 11111-34-5)

Or AMPHITOL 24B (Manufacturer: Kao Corporation, CAS No. 683-10-3).

(Second Reagent)

MES buffer solution 75 mmol/L (pH 7.0)

Potassium ferrocyanide (Manufacturer: Kishida Chemical Co., Ltd., Catalog number: 63532) 0.05 mmol/L 4-Aminoantipyrine (4-AAP) (Manufacturer: Tokyo Chemical Industry Co., Ltd., Catalog number: 6694) 0.75 mmol/L Uricase (Manufacturer: KIKKOMAN CORPORATION, Catalog number: 60199) 0.7 U/mL Surfactant 2.0 w/v %

PLURONIC® TR-704 (Manufacturer: ADEKA CORPORATION, CAS No. 11111-34-5)

Or AMPHITOL 24B (Manufacturer: Kao Corporation, CAS No. 683-10-3).

(Blood Sample to be Measured)

The bilirubin-added serum was prepare by adding ditaurobilirubin (Manufacturer: Promega) to the pool serum so that the concentration of the ditaurobilirubin in the serum was at 50 mg/dL. The hemoglobin-added serum was prepared by adding hemoglobin (derived from hemocyte) to the pool serum so that the concentration of the hemoglobin in the serum was at 500 mg/dL.

(Measurement Method)

Hitachi 7170 model automatic analyzer was used, and the first reaction and the second reaction were performed, respectively in a liquid volume ratio of 5.0 µL of the specimen, 200 µL of the first reagent and 100 µL of the second reagent at 37° C. for 5 minutes, and the absorbance at 600 nm main wavelength/800 nm complementary wavelength was measured with an endpoint method.

The uric acid concentration in each blood sample was obtained with comparison to the standard fluids having known concentrations (ANACERAM UA-E standard fluid, the same shall apply hereinafter) (Manufacturer: SEKISUI MEDICAL CO., LTD., Catalog number: 154966).

(Method for Confirming Effect)

The ratio of the measured value of the uric acid concentration in each blood sample was calculated and expressed in percent of the measured value of the uric acid concentration in the control blood sample, and thereby a relative value for the avoidance degree of the influences of bilirubin and hemoglobin in each sample was obtained.

(Results)

Comparative Example 2 and Comparative Example 4 in which AMPHITOL 24B was added in the first reagent, were not affected by bilirubin, but strongly affected by hemoglobin regardless of the kind of the surfactant of the second reagent. The relative value in this case was lower than the relative value of Comparative Example 1 not containing a surfactant either in the first reagent or the second reagent.

Comparative Example 3 in which PLURONIC® TR-704 was added both in the first reagent and the second reagent, was not affected by hemoglobin, but strongly affected by bilirubin.

On the contrary to these Comparative Examples 1 to 4, it was confirmed that Example 2 in which PLURONIC® TR-704 was added in the first reagent and AMPHITOL 24B was added in the second reagent, was not affected by bilirubin or hemoglobin, and could avoid the influences of both of bilirubin and hemoglobin at the same time.

TABLE 3

|  | First reagent | Second reagent | Bilirubin-added serum | Hemoglobin-added serum |
| --- | --- | --- | --- | --- |
| Example 2 | TR-704 | 24B | 94.9 | 101.1 |
| Comparative Example 1 | None | None | 68.2 | 98.5 |
| Comparative Example 2 | 24B | 24B | 97.1 | 79.2 |
| Comparative Example 3 | TR-704 | TR-704 | 77.6 | 98.0 |
| Comparative Example 4 | 24B | TR-704 | 97.8 | 80.6 |

In the Table, TR-704 represents PLURONIC® TR-704, 24B represents AMPHITOL 24B and the numbers are percentage values.

The measurement value for the uric acid concentration of the control blood sample is 4.3 mg/dL.

Example 3

Using a uric acid-measurement system, the optimal concentration range of each surfactant was calculated.

(First Reagent)

MES buffer solution 75 mmol/L (pH 7.0)

TOOS (Manufacturer: Dojindo Molecular Technologies, Inc., Catalog number: OC13) 0.75 mmol/L POD (Manufacturer: TOYOBO CO., LTD., Catalog number: PEO-301) 3 U/mL Surfactant 2.0 w/v %

PLURONIC® TR-704 (Manufacturer: ADEKA CORPORATION, CAS No. 11111-34-5).

(Second Reagent)

MES buffer solution 75 mmol/L (pH 7.0)

Potassium ferrocyanide (Manufacturer: Kishida Chemical Co., Ltd., Catalog number: 63532) 0.05 mmol/L 4-Aminoantipyrine (Manufacturer: Tokyo Chemical Industry Co., Ltd., Catalog number: 6694) 0.75 mmol/L Uricase (Manufacturer: KIKKOMAN CORPORATION, Catalog number: 60199) 0.7 U/mL Surfactant 2.0 w/v %

AMPHITOL 24B (Manufacturer: Kao Corporation, CAS No. 683-10-3)

(Blood Sample to be Measured)

The bilirubin-added serum was prepare by adding ditaurobilirubin (Manufacturer: Promega) to the pool serum so that the concentration of the ditaurobilirubin in the serum was at 40 mg/dL. The hemoglobin-added serum was prepared by adding hemoglobin (derived from hemocyte) to the pool serum so that the concentration of the hemoglobin in the serum was at 400 mg/dL.

(Control Blood Sample)

Saline in a volume equivalent to the added volume of ditaurobilirubin or hemoglobin at the time of the preparation of the blood sample to be measured was added to the pool serum, which was used as the control blood sample.

(Measurement Method)

Hitachi 7170 model automatic analyzer was used, and the first reaction and the second reaction were performed, respectively at 37° C. for 5 minutes, in a liquid volume ratio of and 5.0 µL of the specimen, 200 µL of the first reagent, and 100 µL of the second reagent, and the absorbance at 600 nm main wavelength/800 nm complementary wavelength was measured with an endpoint method.

The uric acid concentration in each blood sample was obtained with comparison to the standard fluids having known concentrations.

(Method for Confirming Effect)

The ratio of the measured value of the uric acid concentration in each blood sample was calculated and expressed in percent of the measured value of the uric acid concentration in the control blood sample, and thereby a relative value (recovery rate (%)) for the avoidance degree of the influences of bilirubin and hemoglobin in each sample was obtained. When the recovery rate was within ±10%, it was judged that it was effective.

(Results)

The optimal concentration range of each surfactant was investigated. As a result, 0.1% to 10% for PLURONIC®, which is a non-ionic surfactant, and 0.5% to 10% for AMPHITOL, which is an amphoteric surfactant, showed the effects of the invention. Particularly, the effects of the invention were prominent with 0.5 to 1.0% of PLURONIC®, which is a non-ionic surfactant, and 2.0 to 10% of AMPHITOL, which is an amphoteric surfactant.

TABLE 4

| | | Pluronic TR-704 | | | | | | | | |
|---|---|---|---|---|---|---|---|---|---|---|
| | | AMPHITOL | 0% | | | | | | 0.1% | |
| | | 24B | 0% | 0.1% | 0.5% | 1% | 2% | 10% | 0% | 0.1% | 0.5% |
| Recovery rate (%) | Bilirubin (mg/dL) | 0 | 100.0 | 100.0 | 100.0 | 100.0 | 100.0 | 100.0 | 100.0 | 100.0 | 100.0 |
| | | 10 | 94.1 | 94.1 | 100.0 | 100.0 | 100.0 | 98.0 | 92.3 | 92.3 | 98.0 |
| | | 20 | 86.3 | 86.3 | 98.0 | 98.0 | 98.0 | 98.0 | 84.6 | 84.6 | 96.1 |
| | | 30 | 78.4 | 80.4 | 96.0 | 98.0 | 98.0 | 96.0 | 78.8 | 76.9 | 94.1 |
| | | 40 | 70.6 | 72.5 | 96.0 | 96.0 | 98.0 | 96.0 | 71.2 | 71.2 | 92.2 |
| | Hemoglobin (mg/dL) | 0 | 100.0 | 100.0 | 100.0 | 100.0 | 100.0 | 100.0 | 100.0 | 100.0 | 100.0 |
| | | 100 | 98.0 | 98.0 | 96.1 | 98.0 | 96.1 | 98.0 | 98.1 | 98.0 | 96.2 |
| | | 200 | 100.0 | 100.0 | 98.0 | 100.0 | 96.1 | 98.0 | 98.1 | 100.0 | 98.1 |
| | | 300 | 98.0 | 98.0 | 98.0 | 96.0 | 94.1 | 98.0 | 98.1 | 100.0 | 98.1 |
| | | 400 | 98.0 | 98.0 | 96.1 | 96.0 | 92.2 | 96.0 | 98.1 | 100.0 | 96.2 |

| | | Pluronic TR-704 | | | | | | | | |
|---|---|---|---|---|---|---|---|---|---|---|
| | | AMPHITOL | 0.1% | | | 0.5% | | | | |
| | | 24B | 1% | 2% | 10% | 0% | 0.1% | 0.5% | 1% | 2% | 10% |
| Recovery rate (%) | Bilirubin (mg/dL) | 0 | 100.0 | 100.0 | 100.0 | 100.0 | 100.0 | 100.0 | 100.0 | 100.0 | 100.0 |
| | | 10 | 98.0 | 100.0 | 98.0 | 94.1 | 94.1 | 100.0 | 98.0 | 100.0 | 100.0 |
| | | 20 | 98.0 | 98.0 | 98.0 | 88.2 | 88.2 | 96.0 | 98.0 | 98.0 | 98.0 |
| | | 30 | 98.0 | 98.0 | 96.1 | 82.4 | 82.4 | 94.0 | 96.1 | 98.0 | 98.0 |
| | | 40 | 96.1 | 96.1 | 94.1 | 74.5 | 76.5 | 92.0 | 94.1 | 96.1 | 96.0 |
| | Hemoglobin (mg/dL) | 0 | 100.0 | 100.0 | 100.0 | 100.0 | 100.0 | 100.0 | 100.0 | 100.0 | 100.0 |
| | | 100 | 98.1 | 98.0 | 96.1 | 98.1 | 100.0 | 98.0 | 98.0 | 98.0 | 96.1 |
| | | 200 | 98.1 | 98.0 | 98.0 | 98.1 | 100.0 | 100.0 | 100.0 | 102.0 | 98.0 |
| | | 300 | 98.1 | 96.1 | 96.1 | 98.1 | 100.0 | 98.0 | 100.0 | 100.0 | 98.0 |
| | | 400 | 96.2 | 96.1 | 96.1 | 98.1 | 100.0 | 98.0 | 100.0 | 102.0 | 98.0 |

| | | Pluronic TR-704 | | | | | | | | |
|---|---|---|---|---|---|---|---|---|---|---|
| | | AMPHITOL | 1% | | | | | | 2% | |
| | | 24B | 0% | 0.1% | 0.5% | 1% | 2% | 10% | 0% | 0.1% | 0.5% |
| Recovery rate (%) | Bilirubin (mg/dL) | 0 | 100.0 | 100.0 | 100.0 | 100.0 | 100.0 | 100.0 | 100.0 | 100.0 | 100.0 |
| | | 10 | 94.1 | 94.1 | 98.0 | 100.0 | 98.0 | 100.0 | 96.1 | 96.1 | 98.0 |
| | | 20 | 90.2 | 90.2 | 96.0 | 98.0 | 98.0 | 98.0 | 90.2 | 92.2 | 96.0 |
| | | 30 | 84.3 | 86.3 | 96.0 | 96.0 | 96.1 | 98.0 | 86.3 | 86.3 | 94.0 |
| | | 40 | 78.4 | 78.4 | 90.0 | 94.0 | 96.1 | 96.0 | 82.4 | 82.4 | 90.0 |
| | Hemoglobin (mg/dL) | 0 | 100.0 | 100.0 | 100.0 | 100.0 | 100.0 | 100.0 | 100.0 | 100.0 | 100.0 |
| | | 100 | 98.0 | 96.2 | 100.0 | 96.1 | 98.0 | 98.0 | 98.0 | 98.0 | 98.0 |
| | | 200 | 100.0 | 100.0 | 102.0 | 100.0 | 100.0 | 100.0 | 100.0 | 100.0 | 98.0 |
| | | 300 | 100.0 | 98.1 | 100.0 | 100.0 | 102.0 | 100.0 | 98.0 | 100.0 | 98.0 |
| | | 400 | 98.0 | 98.1 | 100.0 | 100.0 | 103.9 | 102.0 | 100.0 | 100.0 | 98.0 |

| | | Pluronic TR-704 | | | | | | | | |
|---|---|---|---|---|---|---|---|---|---|---|
| | | AMPHITOL | 2% | | | 10% | | | | |
| | | 24B | 1% | 2% | 10% | 0% | 0.1% | 0.5% | 1% | 2% | 10% |
| Recovery rate (%) | Bilirubin (mg/dL) | 0 | 100.0 | 100.0 | 100.0 | 100.0 | 100.0 | 100.0 | 100.0 | 100.0 | 100.0 |
| | | 10 | 98.0 | 100.0 | 100.0 | 100.0 | 98.0 | 100.0 | 98.0 | 100.0 | 100.0 |
| | | 20 | 96.1 | 98.0 | 100.0 | 98.0 | 96.0 | 98.0 | 96.0 | 98.0 | 100.0 |
| | | 30 | 94.1 | 96.1 | 98.0 | 95.9 | 94.0 | 95.9 | 94.0 | 98.0 | 97.9 |
| | | 40 | 92.2 | 94.1 | 98.0 | 93.9 | 92.0 | 93.9 | 92.0 | 95.9 | 97.9 |
| | Hemoglobin (mg/dL) | 0 | 100.0 | 100.0 | 100.0 | 100.0 | 100.0 | 100.0 | 100.0 | 100.0 | 100.0 |
| | | 100 | 98.0 | 98.0 | 98.0 | 100.0 | 98.0 | 98.0 | 98.0 | 100.0 | 100.0 |
| | | 200 | 100.0 | 102.0 | 102.0 | 102.0 | 100.0 | 100.0 | 100.0 | 102.0 | 104.2 |
| | | 300 | 100.0 | 102.0 | 105.9 | 102.0 | 100.0 | 100.0 | 100.0 | 102.0 | 106.3 |
| | | 400 | 100.0 | 102.0 | 107.8 | 102.0 | 100.0 | 100.0 | 100.0 | 102.0 | 108.3 |

Example 4

Using a uric acid-measurement system, a surfactant usable for the invention was investigated.
The kind and the concentration of the surfactants added in the first reagent and the second reagent were as described in Table 5, and the measurement reagent was prepared.
(First Reagent)
  MES buffer solution 75 mmol/L (pH 7.0)
  TOOS (Manufacturer: Dojindo Molecular Technologies, Inc., Catalog number: OC-13) 0.75 mmol/L
  POD (Manufacturer: KIKKOMAN CORPORATION, Catalog number: PEO-301) 3 U/mL
  Surfactant
(Second Reagent)
  MES buffer solution 75 mmol/L (pH 7.0)
  Potassium ferrocyanide (Manufacturer: Kishida Chemical Co., Ltd., Catalog number: 63532) 0.05 mmol/L
  4-Aminoantipyrine (Manufacturer: Tokyo Chemical Industry Co., Ltd., Catalog number: 6694) 0.75 mmol/L
  Uricase (Manufacturer: KIKKOMAN CORPORATION, Catalog number: 60199) 0.7 U/mL
  Surfactant
(Blood Sample to be Measured)
The bilirubin-added serum was prepare by adding ditaurobilirubin (Manufacturer: Promega) to the pool serum so that the concentration of the ditaurobilirubin in the serum was at 50 mg/dL. The hemoglobin-added serum was prepared by adding hemoglobin (derived from hemocyte) to the pool serum so that the concentration of the hemoglobin in the serum was at 500 mg/dL.
(Measurement Method)
Hitachi 7170 model automatic analyzer was used, and the first reaction and the second reaction were performed, respectively at 37° C. for 5 minutes, in a liquid volume ratio of 5.0 μL of the specimen, 200 μL of the first reagent and 100 μL of the second reagent, and the absorbance at 600 nm main wavelength/800 nm complementary wavelength was measured with an endpoint method.
The uric acid concentration in each blood sample was obtained with comparison to the standard fluids having known concentrations.
(Method for Confirming Effect)
The ratio of the measured value of the uric acid concentration in each blood sample was calculated and expressed in percent of the measured value of the uric acid concentration in the control blood sample, and thereby a relative value (recovery rate (%)) for the avoidance degree of the influences of bilirubin and hemoglobin in each sample was obtained. When the recovery rate was within ±10%, it was judged that it was effective.
(Results)
As shown in Table 5, it was found that, even in a case where non-ionic surfactants other than PLURONIC® TR-704 were used, it was possible to avoid the influences of both of bilirubin and hemoglobin. When AMPHITOL 20N, an N-oxide type, was used as the amphoteric surfactant instead of AMPHITOL 24B, a betaine-type, it was shown that the sample was greatly affected by hemoglobin. AMPHITOL 20N was conventionally considered to be capable of avoiding the influence of hemoglobin or bilirubin, respectively. However, according to the investigation of the inventors, it was revealed that the effect was not in a practical level. On the other hand, it was found that cocamidopropyl betaine, which is an amidoalkyl betaine; sodium cocoamphoacetate, which is a 2-alkyl-N-carboxymethyl-N-hydroxyethylimidazolinium betaine; and 3-[(3-cholamidopropyl)dimethylamino]-1-propane sulfonate, which is a sulfobetaine; had similar effects to amidobetaine.

TABLE 5

| Category | Compound name | Kind | | | | | Concentration (%) | |
| | | Trademark | Manufacturer | Bilirubin | Hemoglobin | Non-ionic surfactant | AMPHITOL 24B |
| | | Non-ionic surfactant | | | | | | |
| --- | --- | --- | --- | --- | --- | --- | --- |
| POE•POP block polymer type | Polyoxyethylene•polyoxypropylene alkyl ether | Pluronic TR-704 | ADEKA | ○ | ○ | 2.0 | 2.0 |
| | Polyoxyethylene•polyoxypropylene alkyl ether | Pluronic TR-702 | ADEKA | ○ | ○ | 2.0 | 2.0 |
| | Polyoxyethylene•polyoxypropylene alkyl ether | Pluronic F-108 | ADEKA | ○ | ○ | 2.0 | 2.0 |
| | Polyoxyethylene•polyoxypropylene alkyl ether | Pluronic P-85 | ADEKA | ○ | ○ | 2.0 | 2.0 |
| | Polyoxyethylene•polyoxypropylene glycol | EPAN 680 | DAI-ICHI KOGYO SEIYAKU | ○ | ○ | 2.0 | 2.0 |
| | Polyoxyethylene•polyoxypropylene glycol | EPAN U103 | DAI-ICHI KOGYO SEIYAKU | ○ | ○ | 2.0 | 2.0 |
| Alcohol type (ether type) | Polyoxyethylene lauryl ether | NIKKOL BL-25 | Nikko Chemicals | ○ | ○ | 1.0 | 0.5 |
| | Polyoxyethylene cetyl-stearyl ether | EMULGEN 220 | Kao Corporation | ○ | ○ | 1.0 | 0.5 |
| | Polyoxyethylene oleyl ether | EMULGEN 420 | Kao Corporation | ○ | ○ | 1.0 | 0.5 |
| | Polyoxyethylene alkyl ether | NIKKOL BT-9 | Nikko Chemicals | ○ | ○ | 1.0 | 0.5 |
| | Polyoxyethylene lauryl ether | NIKKOL BL-4.2 | Nikko Chemicals | ○ | x | 1.0 | 0.5 |

TABLE 5-continued

| | | | | | | Pluronic TR-704 | Amphoteric surfactant |
|---|---|---|---|---|---|---|---|
| Alkyl phenol type | Polyoxyethylene tribenzylphenyl ether | EMULGEN B66 | Kao Corporation | o | o | 1.0 | 0.5 |
| | Polyoxyethylene nonylphenyl ether | NIKKOL NP-10 | Nikko Chemicals | o | o | 1.0 | 0.5 |
| | Polyoxyethylene nonylphenyl ether | NIKKOL NP-15 | Nikko Chemicals | o | o | 1.0 | 0.5 |
| | Polyoxyethylene nonylphenyl ether | NIKKOL NP-20 | Nikko Chemicals | o | o | 1.0 | 0.5 |
| | Polyoxyethylene dodecylphenyl ether | NOIGEN EA-143 | DAI-ICHI KOGYO SEIYAKU | o | o | 1.0 | 0.5 |
| | Polyoxyethylene octylphenyl ether | Triton X-100 | Sigma | o | o | 1.0 | 0.5 |
| Glycoester | Polyoxyethylene sorbitan monolaurate | Tween 20 | Wako Pure Chemical | o | o | 1.0 | 0.5 |
| Glycoamide | Decanoyl-N-methylglucamide | MEGA-9 | Dojindo | x | o | 1.0 | 0.5 |

| Amphoteric surfactant | | | | | | Pluronic TR-704 | Amphoteric surfactant |
|---|---|---|---|---|---|---|---|
| Betaine type | Lauryl betaine | AMPHITOL 24B | Kao Corporation | o | o | 2.0 | 2.0 |
| | Lauryl betaine | AMPHITOL 20BS | Kao Corporation | o | o | 2.0 | 2.0 |
| | Cocamidopropyl betaine | ENAGICOL C30B | Lion | o | o | 2.0 | 2.0 |
| | Na cocoampho acetate | ENAGICOL C40H | Lion | o | o | 2.0 | 2.0 |
| N-oxide | Lauryl dimethylamine oxide | AMPHITOL 20N | Kao Corporation | x | x | 2.0 | 2.0 |
| Bile acid salt | 3-[(3-cholamidopropyl)dimethylamino]-1-propane sulfonate | CHAPS | MoBiTec | o | o | 2.0 | 2.0 |

Example 5

(First Reagent)

MES buffer solution 75 mmol/L (pH 7.0)

TOOS (Dojindo Molecular Technologies, Inc.: Catalog number: OC-13) 0.75 mmol/L

Each surfactant 2.0 w/v %

(Second Reagent)

MES buffer solution 75 mmol/L (pH 7.0)

Uricase (Manufacturer: KIKKOMAN CORPORATION, Catalog number: 60199) 2.3 U/mL (Third Reagent)

MES buffer solution 75 mmol/L (pH 7.0)

POD (Manufacturer: TOYOBO CO., LTD., Catalog number: PEO-301) 8.6 U/mL

Potassium ferrocyanide (Manufacturer: Kishida Chemical Co., Ltd., Catalog number: 63532) 0.05 mmol/L 4-Aminoantipyrine (Manufacturer: Tokyo Chemical Industry Co., Ltd., Catalog number: 6694) 0.75 mmol/L Each surfactant 2.0 w/v %

(Measurement Method)

Hitachi 7170 model automatic analyzer was used, 5.0 μL of the specimen, and the first reaction, the second reaction and the third reaction were performed, respectively at 37° C. for 5 minutes (15 minutes reaction in total), in a liquid volume ratio of 200 μL of the first reagent, 30 μL of the second reagent, and 70 μL of the third reagent, and the absorbance at 600 nm main wavelength/800 nm complementary wavelength was measured with an endpoint method.

The uric acid concentration in each blood sample was obtained with comparison to the standard fluids having known concentrations.

TABLE 6

| | First reagent | Third reagent | Bilirubin-added serum | Hemoglobin-added serum |
|---|---|---|---|---|
| Example 5 | TR-704 | 24B | 93.2 | 100 |
| Comparative Example 5 | None | None | 54.5 | 97.7 |
| Comparative Example 6 | TR-704 | TR-704 | 84.1 | 95.5 |
| Comparative Example 7 | 24B | 24B | 95.5 | 83.7 |
| Example 7 Comparative Example 8 | 24B | TR-704 | 95.5 | 81.8 |

In the Table, TR-704 represents PLURONIC® TR-704, 24B represents AMPHITOL 24B and the numbers are percentage values.

The measurement value for the uric acid concentration of the control blood sample is 4.4 mg/dL.

(Results)

The procedures of Example 5 and Comparative Examples 5 to 8 can be divided into the first process of bringing a sample liquid containing hemoglobin into contact with a surfactant and a coloring agent, the second process of reacting the sample liquid obtained in the first process with uricase to produce hydrogen peroxide, and the third process of adding POD to the sample liquid obtained in the second process so that hydrogen peroxide oxidatively condensates with the coloring agent to show color. It is considered that the influences of bilirubin and hemoglobin in the invention are avoided by the points that the non-ionic surfactant in the first process does not change the color tone of hemoglobin in the sample liquid, and that the amphoteric surfactant prevents bilirubin from becoming a substrate of POD in the third process. Specifically, it is considered that the substrate and the enzyme are not limited to the substrate contained in the sample liquid and the enzyme specific for the substrate used in the second process, and the effects are also exerted when a substrate other than uric acid or an enzyme other than uricase is used.

The invention claimed is:

1. A method for measuring a substance in a blood sample by an enzymatic method, the method comprising:
   (1) contacting the blood sample with a non-ionic surfactant;
   (2) then contacting a sample contacted with the non-ionic surfactant from (1) with a betaine-type amphoteric surfactant, and
   (3) performing an enzymatic reaction and a color reaction with an oxidizable color reagent at the same time as the contact or after the contact with the betaine-type amphoteric surfactant, wherein the non-ionic surfactant is at least one surfactant selected from the group consisting of a polyoxyethylene polyoxypropylene condensate, polyoxyethylene polyoxypropylene alkyl amine condensate, polyoxyethylene polyoxypropylene diamine condensate, polyoxyethylene alkyl ether, polyoxyethylene alkyl phenyl ether, and polyoxyethylene polyalcohol fatty acid ester, and the amount of the non-ionic surfactant is from 0.1 to 10 w/v %, and wherein the betaine-type amphoteric surfactant is at least one surfactant selected from the group consisting of alkyl betaine and amidoalkyl betaine, and the amount of the betaine-type amphoteric surfactant is from 0.5 to 10 w/v %, wherein the blood sample is plasma or serum, and wherein hemoglobin and bilirubin are highly likely to affect a measurement value of the substance that is measured in the blood sample, and wherein the substance in the blood sample is measured by quantifying hydrogen peroxide produced by the enzyme reaction, with the proviso that the substance to be measured is not hemoglobin nor bilirubin.

2. The method according to claim 1, wherein the enzyme in said enzymatic reaction is an oxidase specific for a substance to be measured or a derivative thereof.

3. The method according to claim 1, wherein the oxidizable color reagent is at least one component which is colored by the reaction with hydrogen peroxide.

4. The method according to claim 1, wherein the non-ionic surfactant and/or the betaine-type amphoteric surfactant reduce the influence of hemoglobin and bilirubin in the blood sample on a measurement value.

5. The method according to claim 1, wherein an enzyme in the enzymatic reaction is selected from the group consisting of uricase, uric acid peroxidase, creatininase, creatinase, sarcosine oxidase, creatine peroxidase, cholesterol oxidase, cholesterol peroxidase, lipoprotein lipase, glycerol kinase, glycerol-3-phosphoric acid oxidase, triglyceride peroxidase, polyamine amidohydrolase, polyamine oxidase, putrescine oxidase, polyamine peroxidase, 3-α-hydroxysteroid dehydrogenase, diaphorase, bile acid peroxidase, 1,5-anhydroglucitoloxidase, pyranose oxidase, 1,5-anhydroglucitol peroxidase, pyruvic acid oxidase, pyruvic acid peroxidase, lactic acid oxidase, lactic acid peroxidase, phospholipase D, choline oxidase, phospholipid peroxidase, urea amidolyase, pyruvate kinase, pyruvic acid oxidase, and urea peroxidase.

6. The method according to claim 1, wherein the non-ionic surfactant is a polyoxyethylene polyoxypropylene condensate represented by the formula (1):

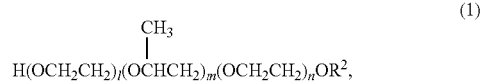

(1)

wherein l and n represent the average addition mole number of ethylene oxide, and m represents the average addition mole number of propylene oxide, and l and n are each a number of from 0 to 250, l+n is 1 or more, and m is a number of from 1 to 250, l and n may be the same or different, $R^2$ represents a hydrogen atom or an alkyl group having from 2 to 20 carbon atoms.

7. The method according to claim 1, wherein the non-ionic surfactant is a polyoxyethylene polyoxypropylene alkyl amine condensate or polyoxyethylene polyoxypropylene diamine condensate represented by the formula (2) to (5):

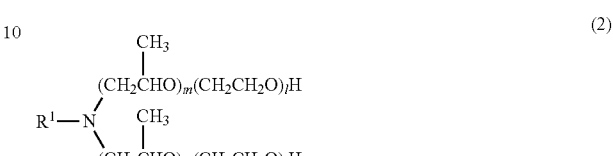

(2)

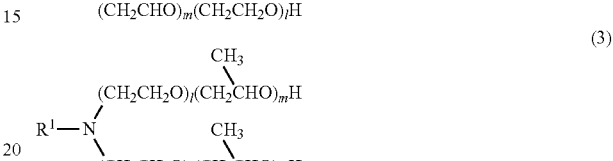

(3)

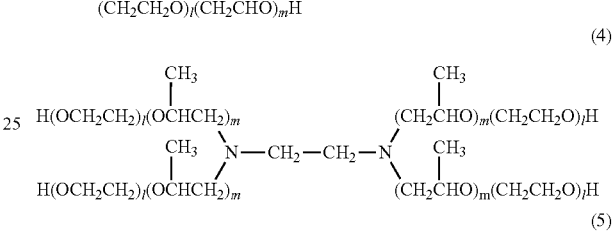

(4)

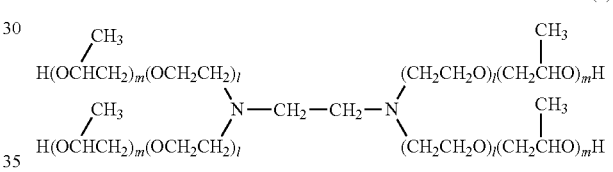

(5)

wherein $R^1$ represents an alkyl group having from 2 to 20 carbon atoms, l represents a number of from 1 to 150 and m represents a number of from 1 to 100.

8. The method according to claim 1, wherein the non-ionic surfactant is polyoxyethylene C10-C24 alkyl ether having from 5 to 80 of polyoxyethylene (POE) addition mole number.

9. The method according to claim 1, wherein the non-ionic surfactant is polyoxyethylene C6-C18 alkyl phenyl ether having from 5 to 80 of POE addition mole number.

10. The method according to claim 1, wherein the non-ionic surfactant is polyoxyethylene polyalcohol fatty acid ester is polyoxyethylene sorbitan fatty acid ester, polyoxyethylene glycerin fatty acid ester, or a mixture thereof.

11. The method according to claim 1, wherein the non-ionic surfactant is is polyoxyethylene sorbitan C8-C24 fatty acid ester having from 3 to 60 of POE addition mole number.

12. The method according to claim 1, wherein the amount of the non-ionic surfactant is from 0.5 to 1.0 w/v %.

13. The method according to claim 1, wherein the amount of the betaine-type amphoteric surfactant is from 0.5 to 2.0 w/v %.

14. The method according to claim 1, wherein the amount of the betaine-type amphoteric surfactant is from 2.0 to 10 w/v %.

* * * * *